United States Patent [19]

Hori et al.

[11] Patent Number: 4,971,451
[45] Date of Patent: Nov. 20, 1990

[54] METHOD FOR MEASURING A GEL-POINT TEMPERATURE

[75] Inventors: Tomoshige Hori, Kitamoto; Kensuke Itoh, Kodaira, both of Japan

[73] Assignee: Snow Brand Milk Products Co., Ltd., Hokkaido, Japan

[21] Appl. No.: 395,791

[22] Filed: Aug. 18, 1989

[30] Foreign Application Priority Data

Aug. 30, 1988 [JP] Japan .................................. 60-216185

[51] Int. Cl.⁵ ............................................. G01N 25/04
[52] U.S. Cl. ...................................... 374/016; 374/25; 374/134; 436/147
[58] Field of Search ................... 374/16, 21, 25, 134, 374/17-20; 436/147; 422/109; 73/64.1

[56] References Cited

U.S. PATENT DOCUMENTS

| | | | |
|---|---|---|---|
| 2,423,687 | 7/1947 | Davis et al. | 374/23 |
| 2,952,152 | 9/1960 | Fisher et al. | 374/24 |
| 3,413,836 | 12/1968 | Nadeau et al. | 374/23 |
| 3,982,420 | 9/1976 | Blevins et al. | 374/17 |
| 4,262,521 | 4/1981 | Beck | 374/23 |
| 4,484,821 | 11/1984 | Willcock | 374/24 |
| 4,611,928 | 9/1986 | Hori et al. | 374/21 |
| 4,663,169 | 5/1987 | Hori et al. | 374/16 |
| 4,762,427 | 8/1988 | Hori et al. | 374/16 |
| 4,770,540 | 9/1988 | Chague et al. | 374/25 |

Primary Examiner—William A. Cuchlinski, Jr.
Assistant Examiner—William C. Dowling
Attorney, Agent, or Firm—Branigan & Butler Griffin

[57] ABSTRACT

A heat-generating element and a fluid temperature measuring element are immersed in a molten or gelled fluid sample to measure continuously both temperature $\Sigma w$ of the said heat-generating element and fluid temperature $\Theta \infty$ during the cooling or heating of the fluid sample at one or several constant cooling or heating rates. An abrupt change in $\Theta w - \Theta \infty$ value is detected to obtain the practical gel-point temperature of a characteristic gel-point temperature, which is defined as the extrapolated gel-point temperature at a cooling or heating rate of zero.

4 Claims, 3 Drawing Sheets

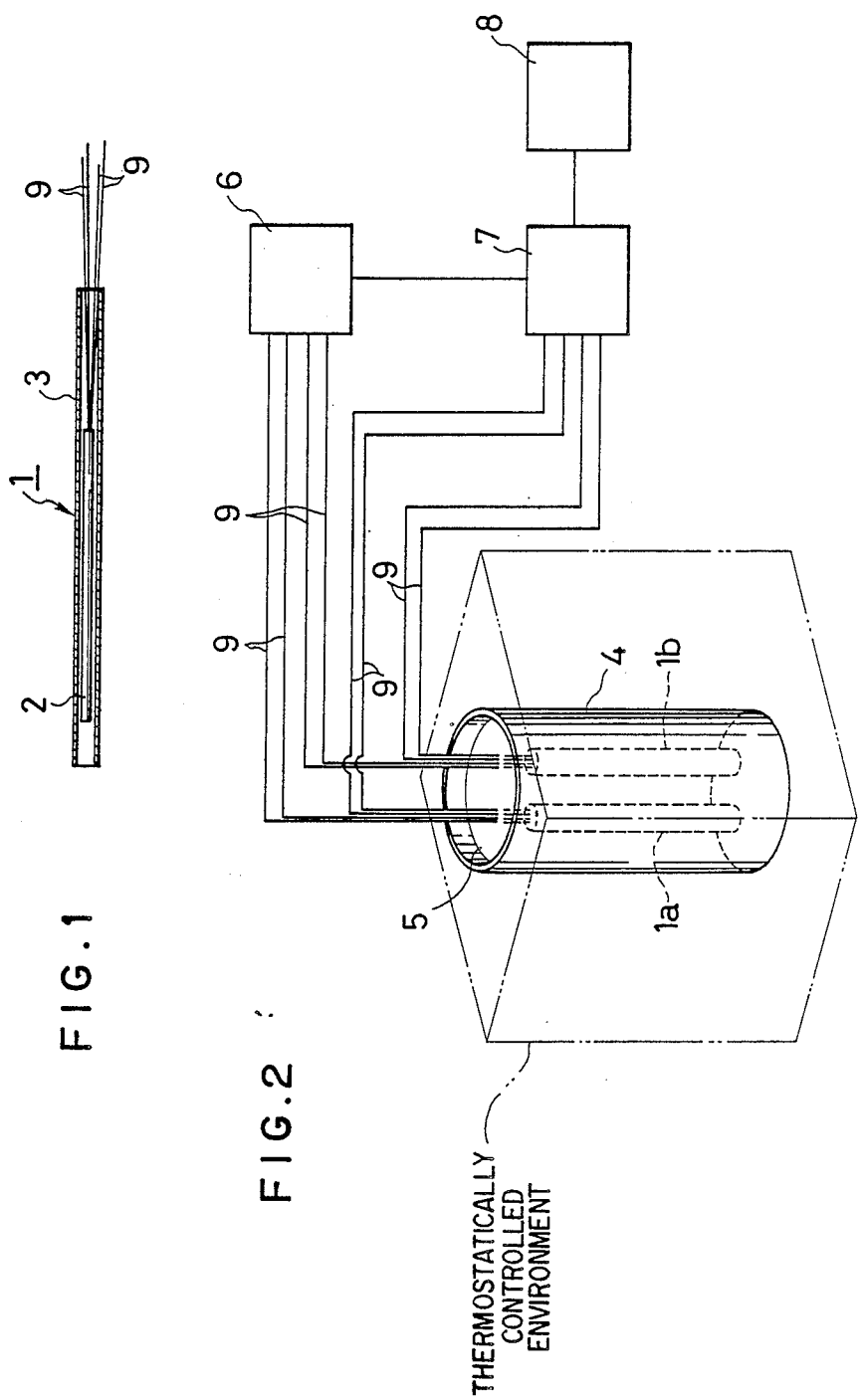

METHOD FOR MEASURING A GEL-POINT TEMPERATURE

BACKGROUND OF THE INVENTION

The present invention relates to a method for measuring gel-point temperatures of gelled and/or molten fluids such as foodstuffs and high molecular compounds.

Industrially, appropriate control of the gel-point temperature of aqueous foodstuffs during manufacturing process is very useful to achieve quality improvement of the respective final products.

The gel-point temperature measurement of prior art includes, (1) The subjective method in which an iron ball is placed on a mass of gel contained within a tube, then the mass of gel is heated while visually observing the iron ball which begins to sink into the mass of gel and a temperature at which the iron ball thus begins to sink into the mass of gel is measured as a gel-point temperature; and (2) The method to determine a process of gelation, e.g., for aqueous solution of starch or the like, in which a change in quantity of transmitted light as a function of a temperature change is measured and a change of physical properties is related to a change of the light quantity (Japanese Disclosure Gazette No. 1979-121190).

Of the well known methods as have been mentioned above, the method utilizing the iron ball is relatively low in measurement accuracy, since, in accordance with this method, the moment at which the iron ball begins to sink is visually observed by a human operator while the method based on the quantity of transmitted light is limited in its application because the object to be measured must be transparent. These methods of prior art accordingly have a common weak point such that it is impossible for these methods to measure gel-point temperatures on a variety of substances.

SUMMARY OF THE INVENTION

An object of this invention is to provide a method by which a gel-point temperature of substantially any substance is measured with high accuracy and in an objective manner.

Accordingly, the present invention resides in a method for measuring a gel-point temperature comprising steps of stationarily providing a heat generating element adapted a generate heat and at the same time to measure a temperature of itself and a fluid temperature measuring element within a quantity of fluid to be measured; continuously measuring factors such as an average temperature $\theta w$ of the heat generating element, a surface temperature $\theta s$ of said heat generating element, a temperature difference between the average temperatures $\theta w$ of said heat generating element and a temperature $\theta_\infty$ of the fluid, a temperature difference between the surface temperature $\theta s$ of said heat generating element and the temperature $\theta_\infty$ of the fluid, and a heat transfer coefficient $\alpha$ at the surface of said heat generating element while a temperature of the fluid to be measured is increased or decreased; and detecting an abrupt change in an average temperature $\theta_f$ of an imaginary layer of stagnant fluid formed around said heat generating element, said average temperature $\theta_f$ being calculated from the measurements set forth above, and thereby determining a gel-point temperature.

Such method of this invention provides affects as follow:

A. Gel-point temperature measurement is also possible even when the fluid to be measured is accompanied with no significant endothermic reaction and/or is opaque;

B. Gel-point temperature measurement is possible selectively at various temperature changing rates and it is possible to calculate a gel-point temperature at the temperature changing rate of zero (i.e., a reference value representing a gelation characteristic of this fluid) from the measurements obtained at various temperature changing rates;

C. Instead of relying upon visual observation by a human operator, a gel-point temperature can be derived from a viscosity change of the fluid objectively by the apparatus itself and, therefore, with high accuracy;

D. Both the off-line measurement by fluid sampling and the on-line measurement during the manufacturing process are possible;

E. The method according to this invention is free from structural destruction of gel as has been inevitably caused by the mechanical measuring method of prior art and, therefore, applicable to a fluid for which the gel-point temperature measurement has been difficult due to such structural destruction;

F. Any size of the heat generating element is selective, so that even a small quantity of sample can be subjected to the measurement; and G. The measurement is possible even under special conditions such as high temperature and high pressure.

BRIEF DESCRIPTION OF THE DRAWINGS

The above and other objects of the invention will be seen by reference to the description taken in connection with the accompanying drawings, in which:

FIG. 1 is a sectional view showing an embodiment of the heat generating element used for the method of the invention;

FIG. 2 is a conceptual view of the measuring method according to the invention;

DETAILED DESCRIPTION OF THE INVENTION

Figure 3:
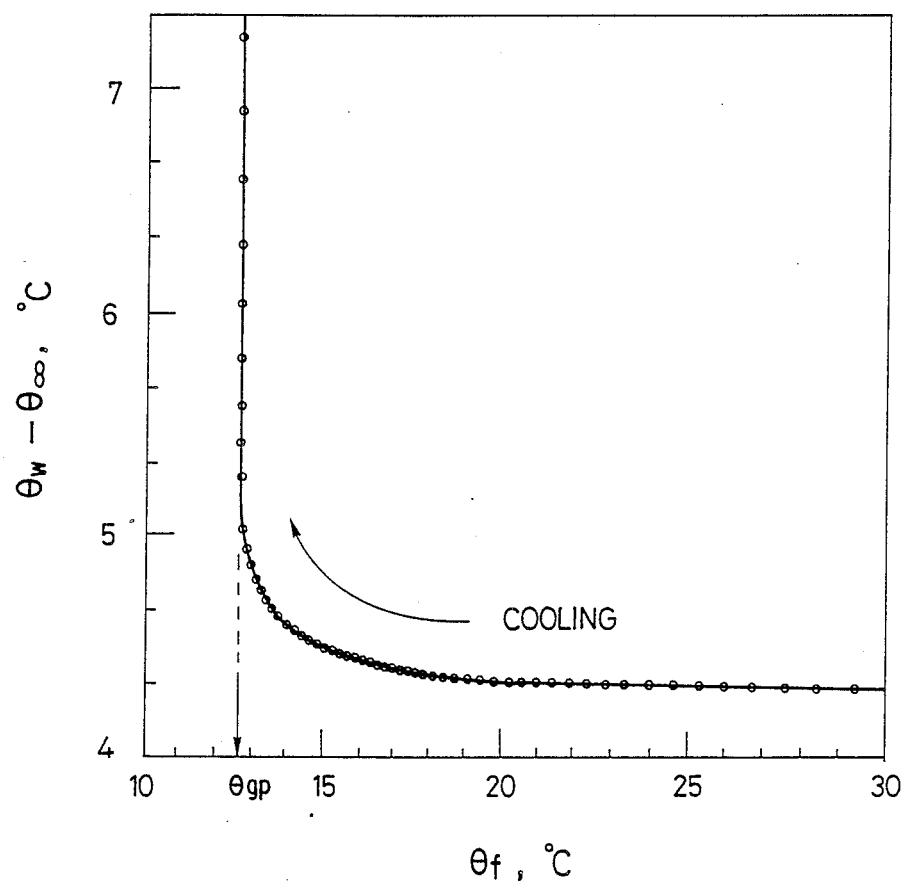
FIG. 3 is a graphic diagram showing a relationship of a differential value between the surface temperature $\theta s$ of said heat generating element stationarily provided in 1% aqueous solution of gelatin which is being cooled and the fluid temperature $\theta_\infty$ with the average temperature $\theta_f$ of said stagnant fluid layer.

As the first step of the method according to the present invention, there is stationarily provided in a mass of molten or gelled fluid a heat generating element adapted to generate heat and at the same time to measure a temperature of itself and a fluid temperature measuring element.

Then, electric resistance values of the respective elements are continuously measured by utilizing the well-known four-terminal method, and thereby factors such as said average temperature $\theta w$ of heat generating element, said surface temperature $\theta s$ of heat generating element, the temperature difference between said average temperature $\theta w$ and said fluid temperature $\theta_\infty$, the temperature difference between said surface temperature $\theta s$ and said fluid temperature $\theta_\infty$, and a heat transfer coefficient $\alpha$ at the surface of said heat generating element so that any significant change in these values may be detected to determine a gel-point temperature. It should be understood that, for a gelled fluid, the measurement may be performed while the mass of said fluid is being heated and, for molten fluid, the measurement may be performed while the mass of said fluid is being cooled.

The average temperature $\theta w$ of heat generating element is obtained by measuring the electric resistance value $Rw$ of the element contained within the heat generating element 1 and then calculating the following equation:

$$\theta w = \frac{-R_1 + \sqrt{R_1^2 - 4R_2(R_0 - R_w)}}{2R_2} \tag{1}$$

and $$Rw = Vw/iw \tag{2}$$

where R0 through R2 represent temperature coefficients of electric resistance.

The fluid temperature $\theta_\infty$ is also calculated from the electric resistance value of the element contained within the thermoresistor 1b. It should be noted here that said thermoresistor may be of a construction identical to that of the heat generating element 1.

As disclosed by the inventors in Japanese Disclosure Gazette No. 1988-132149, it is known that the average temperature $\theta w$ of heat generating element can be used to express the surface temperature $\theta s$ of heat generating element by the following equation:

$$\theta_s = \theta_\infty + k_1(\theta_w - \theta_\infty)k_2 \tag{3}$$

where $k_1$ and $k_2$ represent constants specific value to the heat generating element.

Accordingly, the surface temperature $\theta s$ of heat generating element can be calculated from the average temperature $\theta w$ of the heat generating element and the fluid temperature $\theta_\infty$.

Thus, it is possible to determine or to calculate the average temperature $\theta w$ of the heat generating element, the surface temperature $\theta s$ of the heat generating element, the temperature difference between said average temperature $\theta w$ of the heat generating element and said fluid temperature $\theta_\infty$ and the temperature difference between said surface temperature $\theta s$ of the heat generating element and said fluid temperature $\theta_\infty$.

The heat transfer coefficient $\alpha$ is given by a following equation:

$$\alpha = Q/S(\theta_s - \theta_\infty) \tag{4}$$

where Q represents a heat flux from the heat generating element, S represents a surface area of the heat generating element and $$Q = Rw(iw)^2 \tag{5}$$

The average temperature $\theta w$ of the heat generating element, the surface temperature $\theta s$ of the heat generating element, the temperature difference between said average temperature $\theta w$ of the heat generating element and the fluid temperature $\theta_\infty$, the temperature difference between said surface temperature $\theta s$ of the heat generating element and said fluid temperature $\theta_\infty$, and the heat transfer coefficient $\alpha$ are index values reflecting the kinematic viscosity of the fluid as described in the above-mentioned Japanese Disclosure Gazette No. 1988-132149.

In view of the fact that gelation or melting of fluid is accompanied with a significant change in the viscosity thereof, said index values may be determined while the fluid temperature $\theta_\infty$ is gradually changed, and a point at which said index values significantly change can be detected to determine a gel-point temperature.

In order to achieve a further accurate measurement of the gel-point temperature, the average temperature $\theta_f$ of the stagnant fluid layer can be used instead of the fluid temperature $\theta_\infty$ in the above-mentioned procedure.

Concerning the calculation of $\theta_f$, Sparrow proposed the model of an imaginary layer of stagnant fluid through which heat is transfered only by conduction (Sparrow, E. M. and Gregg, J. L. 1956; Trans. Amer. Soc. Mech. Engrs. 78: 1823–1829). According to this model, the temperature distribution over said stagnant fluid layer is expressed by $$\theta(r) = \frac{\theta_s \ln\left(\frac{d_f}{2|r|}\right) - \theta_\infty \ln\left(\frac{d}{2|r|}\right)}{\ln\left(\frac{d_f}{d}\right)} \tag{6}$$

and $\theta f$ is given as an integrated average temperature of said temperature distribution by $$\theta_f = \frac{\theta_s \ln\left(\frac{d_f}{2}\right) - \theta_\infty \ln\left(\frac{d}{2}\right)}{\ln\left(\frac{d_f}{d}\right)} + \frac{\theta_\infty - \theta_s}{(d_f^2 - d^2)\ln\left(\frac{d_f}{d}\right)} \times \left[d_f^2 \left(\ln\left(\frac{d_f}{2}\right) - \frac{1}{2}\right) - d^2 \left(\ln\left(\frac{d}{2}\right) - \frac{1}{2}\right)\right] \tag{7}$$

The relationship in the equation 7 between $d_f$ and $\delta$ are respectively expressed by following equations:

$$d_f = d + 2\delta \tag{8}$$

$$\delta = \frac{d}{2}\left\{\exp\left(\frac{2\lambda}{\alpha d}\right) - 1\right\} \tag{9}$$

where $\delta$ represents a thickness of said stagnant fluid layer.

Thus the average temperature $\theta_f$ of the stagnant fluid layer is claculated from said diameter d of the heat generating element, the thermal conductivity $\lambda$ of the stagnant fluid, the fluid temperature $\theta_\infty$, the surface temperature $\theta s$ of the heat generating element and the heat transfer coefficient $\alpha$. For an aqueous gel, $\lambda$ is practically constant and can be assumed as 0.6 w/m k.

EXAMPLE 1

Now the experiment procedures conducted by the inventors and the result thereof will be described below as embodiments of the present invention.

In this Example, a change in the average temperature $\theta_f$ of the stagnant fluid layer with respect to the temperature difference between the surface temperature $\theta_s$ of the heat generating element and the fluid temperature $\theta_\infty$ was measured while a molten sample was being cooled, and a significant change was detected to determine a gel-point temperature.

Before a progress of the experiment is described in detail, a particular heat generating element 1 which was used in this example will be explained in reference with FIG. 1. This heat generating element 1 consists of an element 2 comprising platinum wire which is 5 cm long, exhibits a resistance value of approximately 5 Ω at a temperature of 0° C. and is contained within a piece of ceramic pipe, and a piece of stainless pipe 3 having an outer diameter of 2 mm and a length of 10 cm which contains said element 2 fixed therein. As far as this specific embodiment of the heat generating element 1 is concerned, k1 and k2 in the above-mentioned equation 3 were 0.521 and 0.941, respectively.

As shown by FIG. 2, a container 4 was filled with 1% aqueous solution of gelatin and placed in a thermostatically controlled environment so as to maintain said solution at a temperature of approximately 50° C. There was uprightly provided in said aqueous solution a heat generating element 1a and a thermoresistor 1b having a construction identical to that of said heat generating element 1a and both of them were electrically connected by lead wires 9 to a constant DC (direct electric current) source 6, a digital volt meter 7 and a controller 8. Electric resistance values of resistors contained within 1a and 1b, respectively, were continuously measured utilizing the four-terminal method while said aqueous solution 5 was being cooled and thereby the average temperature $\theta w$ of heat generating element as well as the fluid temperature $\theta_\infty$ were continuously measured.

Specifically, the heat generating element 1a was supplied with constant DC (0.4 A in this experiment) causing a self-heating thereof and simultaneously the average temperature $\theta w$ of the heat generating element was derived from the resistance value Rw calculated on the basis of the voltage Vw value and the current value iw. At the same time, the thermoresistor 1b was supplied with feeble constant DC (1 mA in this experiment) and the temperature of the thermoresistor 1b was derived from the resistance value calculated on the basis of the voltage value and the current value thereof as the temperature $\theta_\infty$ of the aqueous solution 5 surrounding said thermoresistor 1b. By the using these values of $\theta w$ and $\theta_\infty$, the surface temperature $\theta s$ of heat generating element was calculated according to the equation 3.

The average temperature $\theta_f$ of the stagnant fluid layer around the heat generating element 1a was calculated utilizing the definition equation 7.

The experiment as has been mentioned above was conducted while the sample solution was being cooled at a rate of 24° C./hr and it was found that, as shown by FIG. 3, the temperature difference $\theta w - \theta_\infty$ abruptly changes at a point substantially corresponding to the stagnant fluid layer average temperature $\theta_f$ of 12.4° C. Based on this result, a gel-point temperature $\theta_{gp}$ of 12.4° C. was obtained for the case in which said 1% aqueous solution of gelatin (Sigma Chemical Co., U.S.A. No. G-2500) was treated at the cooling rate of 24° C./hr.

EXAMPLE 2

Said gel-point temperature was measured at various cooling rates. As seen from FIG. 4, the lower the cooling rate is, the higher the gel-point temperature is. A reference gel-point temperature $\theta_{gp}$ of approximately 27° C. at the cooling rates zero was derived from extrapolation values based on a regression curve of gel-point temperature at the cooling rates of 24° C./hr, 11.2° C./hr and 0.5° C./hr.

While the invention has been particularly shown and described with reference to preferred embodiment thereof, it will be understood by those skilled in the art that the foregoing and other changes in form and details can be made therein without departing from the spirit and scope of the invention.

What is claimed is:

1. A method for measuring the gel-point temperature of a stagnant or flowing fluid comprising the following steps:

(a) immersing a heat-generating element and fluid temperature measuring element in the molten or gelled fluid to be measured;

(b) applying an electric current to the said heat-generating element to heat the element;

(c) cooling the molten fluid or heating the gelled fluid at a constant cooling or heating rate;

(d) measuring both temperature $\theta_w$ of the said heat-generating element and fluid temperature $\theta_\infty$;

(e) calculating temperature difference $\theta_w - \theta_\infty$ between the said heat-generating element and fluid;

(f) calculating temperature $\theta_s$ at the surface of the said heat-generating element by using the experimental formula $$\theta_s = \theta_\infty + k(\theta_w - \theta_\infty)k_2 \qquad (9)$$

where $k_1$ and $k_2$ are numerical constants;

(g) calculating heat transfer coefficient $\alpha$ at the surface of the said heat-generating element by $$\alpha = R_w i_w^2 / S(\theta_s - \theta_\infty) \qquad (10)$$

where $R_w$ is the measured electrical resistance of a hot resistor built into the said heat-generating element, $i_w$ is an electric current applied to the said built-in hot resistor, and S is the surface area of the said heat-generating element;

(h) calculating the thickness of the stagnant fluid layer formed around the said heat-generating element by $$\delta = \frac{d}{2} \left\{ \exp\left(\frac{2\lambda}{\alpha d}\right) - 1 \right\} \qquad (11)$$

where d is the outer diameter of the said heat-generating element and λ is the thermal conductivity of the sample fluid, both d and λ being known constant values for the δ calculation;

(i) calculating average temperature $\theta_f$ of the stagnant fluid layer formed around the said heat-generating element by $$\theta_f = \frac{\theta_s \ln\left(\frac{d_f}{2}\right) - \theta_\infty \ln\left(\frac{d}{2}\right)}{\ln\left(\frac{\alpha_f}{\alpha}\right)} + \frac{\theta_\infty - \theta_s}{(d_f^2 - d^2)\ln\left(\frac{d_f}{\alpha}\right)} \times \qquad (12)$$

$$\left[d_f^2\left\{\ln\left(\frac{d_f}{2}\right) - \frac{1}{2}\right\} - \alpha^2\left\{\ln\left(\frac{d}{2}\right) - \frac{1}{2}\right\}\right]$$

where df is the sum of d and 2 δ;

(j) and detecting an abrupt change, which results from the change in fluid viscosity and heat transfer coefficient at the surface of the said heat-generating element, in the $(\theta_w - \theta_\infty)$ value of the $\theta_f$ vs. $(\theta_w - \theta_\infty)$ curve so that $\theta_f$ temperature of stagnant fluid layer at the point of such abrupt change can be obtained as the gel-point temperature.

2. A method in accordance with claim 1, whereby measured gel-point temperatures at two or more different cooling or heating rates of the same sample fluid are determined, and a calculated extrapolation value of the gel-point temperature at the cooling or heating rate of zero on the basis of the said rate vs. the measured gel-point temperature curve is determined as the characteristic gel-point temperature of the sample fluid.

3. A method in accordance with claim 1, whereby the said heat-generating element is a cylindrical line heat source with a built-in platinum wire for self-heating and temperature self-measurement, the said element being vertically immersed in the fluid sample to be measured.

4. A method in accordance with claim 2, whereby the said heat-generating element is a cylindrical line heat source with a built-in platinum wire for self-heating and temperature self measurement, the said element being vertically immersed in the fluid sample to be measured.

* * * * *

UNITED STATES PATENT AND TRADEMARK OFFICE
CERTIFICATE OF CORRECTION

PATENT NO. : 4,971,451

DATED : November 20, 1990

INVENTOR(S) : Tomoshige HORI and Kensuke ITOH

It is certified that error appears in the above-identified patent and that said Letters Patent is hereby corrected as shown below: TITLE PAGE:

IN THE ABSTRACT:

Line 3 thereof, change "$\Sigma w$" to --$\theta w$--.

Col. 3, line 35, change "$\theta_s = \theta_\infty + k_1(\theta_w - \theta_\infty)k_2$" to --$\theta_s = \theta_\infty + k_1(\theta_w - \theta_\infty)^{k_2}$--

Col. 4, line 68, change "w/mk" to --W/mK--.

Col. 5, line 67, change "$\theta_{9p}$" to --$\theta_{gp}$--.

Col. 6, line 9, change "$\theta_{9p}$" to --$\theta_{gp}$--.

Figure 4:
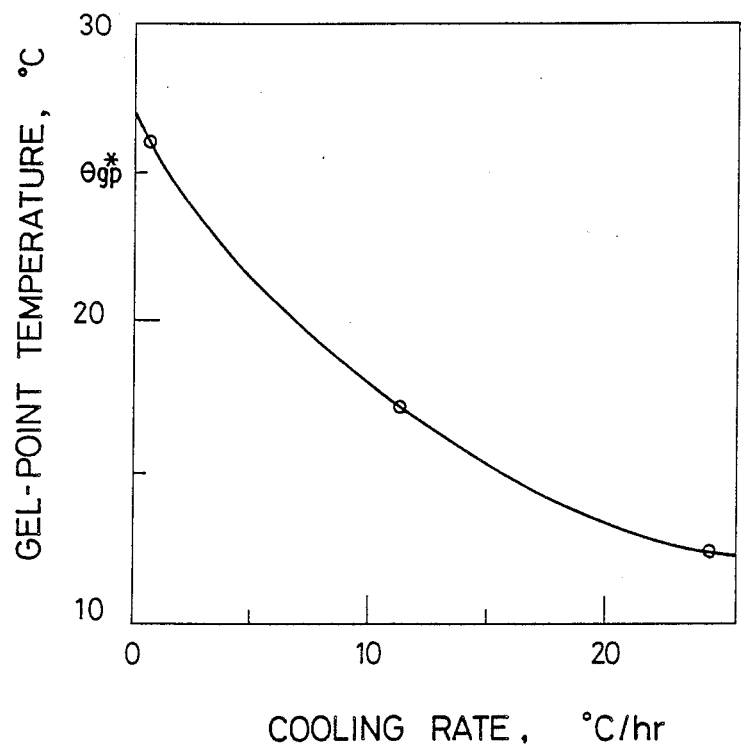
FIG. 4 is a graphic diagram showing a relationship of the cooling rate with the gel-point temperature.
Figure 4:
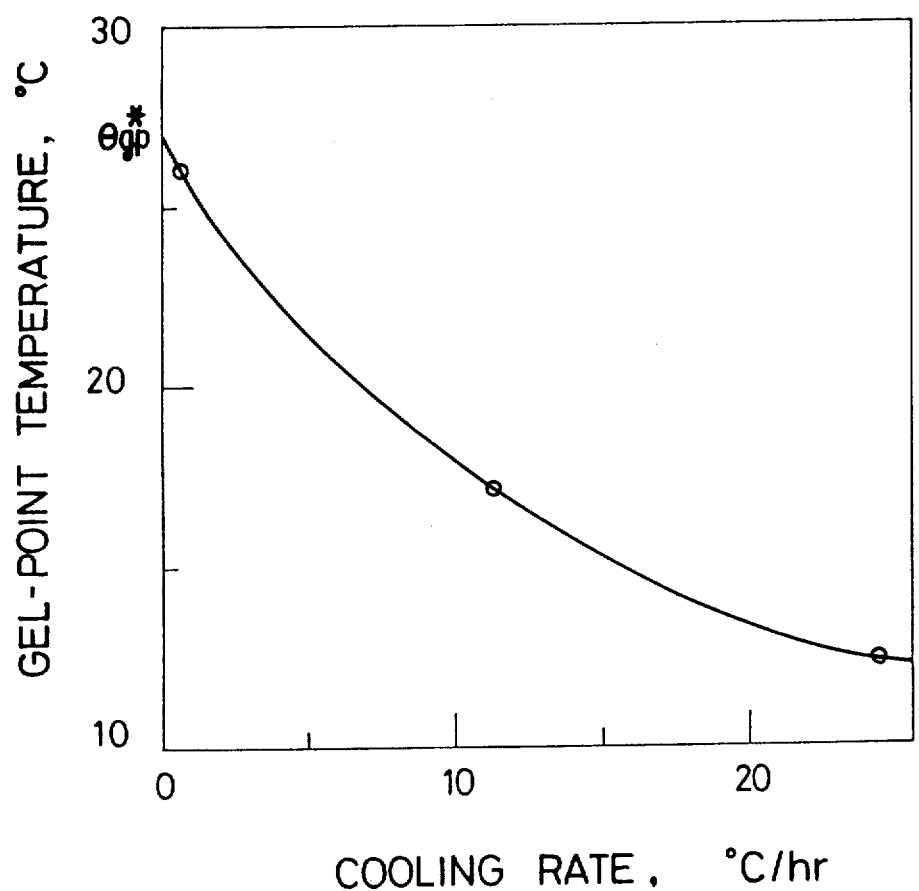

IN THE DRAWINGS:

Sheet 3 of the drawings consisting of Figure 4, should be deleted and substitute therefor the attached corrected Figure 4, as shown on the attached page.

UNITED STATES PATENT AND TRADEMARK OFFICE
CERTIFICATE OF CORRECTION

PATENT NO. : 4,971,451

DATED : November 20, 1990

INVENTOR(S) : Tomoshign HORI and Kensuke ITOH

It is certified that error appears in the above-identified patent and that said Letters Patent is hereby corrected as shown below:

Claim 1 (col. 6), line 18 thereof (line 40 of col. 6), change "$\theta_s = \theta_\infty + k(\theta_w - \theta_\infty)k_2$" to --$\theta_s = \theta_\infty + k_1(\theta_w - \theta_\infty)^{k_2}$--.

Claim 1 (col. 6), line 24 thereof (line 49 of col. 6), change "into" to --in--.

Claim 1 (col. 7), line 39 thereof (line 5 of col. 7), in the formula, change "$\frac{df}{\alpha}$" to --$\frac{df}{d}$-- and change "$\frac{\alpha f}{\alpha}$" to --$\frac{df}{d}$--.

Claim 1 (col. 7), line 40 thereof (line 10 of col. 7), in the formula, change "$\alpha^2$" to --$d^2$--.

Signed and Sealed this

Eighth Day of September, 1992

Attest:

DOUGLAS B. COMER

Attesting Officer   Acting Commissioner of Patents and Trademarks